United States Patent [19]

Clark et al.

[11] 3,976,680

[45] Aug. 24, 1976

[54] PRODUCTION OF AN ESTER OF ONE ENANTIOMER OF AN α-AMINO ACID IN THE FORM OF A SALT WITH AN OPTICALLY ACTIVE ACID

[75] Inventors: John Colin Clark, Gerrards Cross; Joseph Elks, London, both of England

[73] Assignee: Glaxo Laboratories Limited, Greenford, England

[22] Filed: Feb. 23, 1973

[21] Appl. No.: 335,304

[30] Foreign Application Priority Data
Feb. 25, 1972 United Kingdom............... 8902/72
Dec. 22, 1972 United Kingdom............. 59431/72

[52] U.S. Cl. .................... 260/471 A; 260/295 R; 260/295 S; 260/295.5 R; 260/295.5 S; 260/302 A; 260/302 D; 260/307 G; 260/307 H; 260/309; 260/326.14 T; 260/330.5; 260/332.2 A; 260/346.2 R; 260/347.4; 260/468 J; 260/470; 260/479 S; 260/482 R; 260/513 A; 260/519; 260/534 S
[51] Int. Cl.$^2$.................... C07B 19/00; C07B 20/00
[58] Field of Search............. 260/471 A, 309, 347.4, 260/295 R, 295 S, 295.5 R, 295.5 S, 326.2, 302 A, 302 D, 307 G, 307 H, 330.5, 346.2 R, 326.14 T, 332.2 A, 479 S, 482 R, 468 J, 470

[56] References Cited
UNITED STATES PATENTS
3,887,606  6/1975  Phillips et al. ................. 260/471 A

OTHER PUBLICATIONS

Greenstein, J.P., *Chemistry of the Amino Acids* vol. 1 (1961) Pub. by J. Wiley & Sons Co., N.Y., pp. 718–720. c

*Primary Examiner*—Richard L. Raymond
*Attorney, Agent, or Firm*—Bacon & Thomas

[57] ABSTRACT

A process for the production of an ester of one enantiomer of an α-amino acid in the form of a salt with an optically active acid, which comprises reacting an ester of the opposite enantiomer of said α-amino acid (which may be in admixture with an ester of the desired enantiomer) with said optically active acid and an aldehyde or ketone, whereby an ester of the desired enantiomer separates out in the form of the said salt. The free α-amino acid and/or its salts may be obtained by hydrolysis of the ester thus formed.

Optically active α-amino acids and their esters are of use in the synthesis of physiologically active compounds e.g. antibiotics of the penicillin and cephalosporin types. The present invention provides a relatively cheap, high yield process for the production of esters of optically active α-amino acids and for the production of optically active α-amino acids therefrom. Certain novel compounds are disclosed.

18 Claims, No Drawings

PRODUCTION OF AN ESTER OF ONE ENANTIOMER OF AN α-AMINO ACID IN THE FORM OF A SALT WITH AN OPTICALLY ACTIVE ACID

The present invention relates to a novel process for the production of optically active esters of α-amino acids, particularly but not exclusively 2-amino-2-arylacetic acids.

Optically active amino acids and their esters are frequently of use in the synthesis of physiologically active compounds in which optical isomerism is significant in relation to activity. In particular, important antibiotics of the penicillin and cephalosporin series have acylamido side chains derived from such acids. Thus D-2-amino-2-arylacetic acids may be used in the synthesis of 6β-(D-2-amino-2-phenylacetamido) penicillanic acid (ampicillin), 6β-[D-2-amino-2-(p-hydroxyphenyl)acetamido] penicillanic acid (amoxycillin), 7β-(D-2-amino-2-phenylacetamido)-3-methylceph-3-em-4-carboxylic acid (cephalexin), 3-acetoxymethyl-7β-(D-2-amino-2-phenylacetamido) ceph-3-em-4-carboxylic acid (cephaloglycin), 7β-[-D-2-amino-2-(1,4-cyclohexadien-1-yl)-acetamido]-3-methyl-ceph-3-em-4-carboxylic acid (cephradine), and others. Furthermore, naturally occurring α-amino acids are incorporated into nutritional media for intravenous administration in medical conditions where normal oral nutrition is not possible. In order to minimise the solids content of such solutions, it is essential that the α-amino acids be in the optically active form (usually the L-form) which can be utilised by the body in protein synthesis.

It is commonly convenient in relatively largescale production to synthesise amino acids and their esters by non-stereospecific methods and to resolve the racemic product so produced.

Esters of DL-phenylglycine may be obtained readily in good yields from 2-phenylacetic esters, some of which are available in large quantities as waste by-products from the production of semi-synthetic penicillin and cephalosporin antibiotics. It is thus highly desirable commercially to be able to resolve these relatively cheap esters of DL-phenylglycine, and other related esters described hereinafter, successfully and cheaply. Similarly, many naturally occurring amino acids can be synthesised cheaply in the racemic form but then require resolution.

We have previously attempted to resolve such esters by relatively conventional techniques, using optically active acids, and although high resolution efficiencies can be achieved, for economical production of any one optical isomer it is very desirable to find some way of racemising the remaining isomer so that this racemate may itself be subjected to resolution. However, the racemisation conditions usually tend to hydrolyse the ester grouping or, using alcohol solvents which were otherwise very convenient, lead to transesterification. Furthermore some previously suggested processes have involved changes of solvent and these are undesirable.

We have found that these problems can be avoided by providing a system in which the unwanted isomer is racemised in situ while the desired isomer is continuously removed from solution by the resolving agent.

In this way, one enantiomer can be converted into the opposite enantiomer and a racemic mixture may thus be converted into a single optically active form. In practice, this racemisation/resolution process may be rather slow and in some cases it may be preferable simply to enrich the product with respect to one optical isomer. We have found, however, that α-amino acids carrying an aryl substituent, particularly in the α-position, are converted especially rapidly and in this case virtually all of the DL-starting material can be converted into the required isomer in an economical time. The starting material may be the L-isomer, when the D-isomer is the required product or vice versa or a mixture of the two isomers may be used.

Our new method is based on the finding that Schiff bases of the above esters are more readily racemised than the parent esters and usually exist in equilibrium therewith. We have further found that the Schiff bases tend not to form insoluble salts with the resolving acids such as tartaric acid and in consequence, if a DL-ester is partially converted in solution into a Schiff base in the presence of a resolving acid, such as tartaric acid, an equilibrium is eventually reached out of which the required optically active amino acid ester is separated in the form of its salt. In the equilibration process the Schiff base of the other isomer however will continuously be racemised.

Schiff bases of amino acids are generally regarded as optically stable. It is thus surprising that the present process produces the high resolution efficiencies which are desired.

The Schiff base is formed by reaction of the parent ester or a salt thereof with an aldehyde or ketone. The optically active acid may be present during this reaction and may indeed be introduced together with the ester as a salt thereof, or may be added subsequently.

According to one feature of the present invention there is provided a process for the production of an ester of one enantiomer of an α-amino acid in the form of a salt with an optically active acid, which comprises reacting an ester of the opposite enantiomer of said α-amino acid (which may be in admixture with an ester of the desired enantiomer) with said optically active acid and an aldehyde or ketone, whereby an ester of the desired enantiomer separates out in the form of the said salt.

The α-amino acids which are conveniently used in the process of the present invention include compounds of the formula:

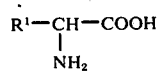

wherein $R^1$ represents an optionally substituted alkyl, aralkyl, aryl or cycloalkyl group. Preferred alkyl groups include straight or branched chain $C_{1-6}$ alkyl groups, which may if desired contain a sulphur or oxygen atom or an NH group or a $>C=C<$ group in the chain, and/or which may if desired contain conventional substituents found in amino acids such as esterified carboxyl (especially alkoxycarbonyl), carbamoyl, thio, etherified thio, hydroxyl or etherified hydroxyl groups or further amino or carboxyl groups. The alkyl portion of an aralkyl group may be similarly modified. Cycloalkyl groups may, if desired, contain one or two double bonds; thus $R^1$ may, for example, represent the cyclohexa-1,4-dien-1-yl group. The term "aryl", both in relation to aryl groups per se and also as part of an aralkyl group, includes not only carbocyclic groups but also heterocyclic aryl groups containing at least one hetero atom selected from nitrogen, sulphur and oxygen such as imidazolyl e.g. 2-or 4-imidazolyl; thien-2-yl; thien-3-yl; furyl e.g. fur-2-yl; pyridyl e.g. pyrid-3-yl; pyrrolyl or N-substituted pyrrolyl e.g. N-methyl pyrrolyl; isothiazolyl; thiadiazolyl; oxadiazolyl; 3- or 4-isoxazolyl; substituted 3- or 4-isoxazolyl e.g. 3-aryl-5-methyl isoxazol-4-yl, the aryl group being, for example, phenyl or halophenyl; and fused heterocyclic groups containing at least one hetero atom selected from nitrogen, sulphur and oxygen e.g. benzothienyl such as benzothien-3-yl, benzofuryl or indolyl such as 2- or 3- indolyl.

It will thus be seen that the process of the present invention is generally applicable to the esters of α-amino acids including for example the esters of naturally occurring α-amino acids such as alanine, valine, leucine, phenylalanine, tyrosine, serine, cysteine, methionine, tryptophan, aspartic acid, glutamic acid, lysine and histidine.

In view of the excellent results which may be obtained with aromatic amino acids, however, $R^1$ preferably represents phenyl and phenyl substituted by, for example, hydroxy; alkoxy e.g. methoxy; acyloxy e.g. acetoxy or benzyloxycarbonyloxy; halogen e.g. chlorine; or lower alkyl e.g. methyl. Thus $R^1$ may be, for example, m-or p-hydroxyphenyl, m- or p-methoxyphenyl, m- or p-chlorophenyl, m-tolyl, etc., or a di- or poly-cyclic group such as α- or β-naphthyl. Particularly preferred $R^1$ groups are unsubstituted phenyl and p-hydroxyphenyl.

The α-amino acid esters may conveniently be represented by the formula

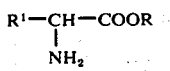
                                                          II where $R^1$ has the above meaning and R represents an unsubstituted or substituted alkyl group with 1–6 carbon atoms, an unsubstituted or substituted cycloalkyl group with 5 or 6 carbon atoms, an aralkyl group or an aryl group. Thus R may be for example methyl, ethyl, isopropyl, butyl, isobutyl, hydroxyalkyl, cyclohexyl, benzyl, benzhydryl or phenyl. Where $R^1$ represents an aryl group, especially an unsubstituted phenyl or p-hydroxyphenyl group, R preferably represents a $C_{1-4}$ alkyl group especially a methyl or ethyl group.

Before the racemisation/resolution process of the present invention is effected it may be necessary to protect any reactive substituents in the $R^1$ group, and subsequently remove such protecting groups. Thus, for example, protection of reactive substituents is particularly necessary with regard to certain of the naturally occurring α-amino acids. Any thiol groups and any additional carboxyl or amino groups will usually require protection. Thiol groups may, for example, be benzylated, carboxyl groups may, for example, be esterified with the same esterifying group as on the carboxyl group bonded to the asymmetric carbon atom or with a different esterifying group and amino groups may, for example, be protected by acylation e.g. N-acetylation or N-benzoylation. Hydroxyl groups present in the compound of formula II e.g. where $R^1$ is p-hydroxyphenyl may also be protected, which protection may be effected, for example, by the use of benzyloxycarbonyloxy group or by etherification.

The aldehyde or ketone may in general be represented by the formula

                                              III where $R^2$ and $R^3$, which may be the same or different, each represents hydrogen or an aliphatic, araliphatic, aromatic or heterocyclic group, e.g. an alkyl group or a monocyclic aralkyl or aryl group, which may carry substituents such as nitro or alkoxy groups. Examples include acetaldehyde, benzaldehyde, anisaldehyde, p-nitrobenzaldehyde, formaldehyde, 2-formylthiophene, furfural, pyridoxal, acetophenone, methyl ethyl ketone, methyl isobutyl ketone and acetone. $R^2$ and $R^3$ may also be joined together as in a cycloalkanone such as cyclohexanone or cyclopentanone. Simple derivatives of aldehydes and ketones such as acetals, hemiacetals, ketals and hemiketals may be used in place of the aldehyde or ketone.

The optically active resolving acid is preferably tartaric acid, more especially (+)-tartaric acid but diesters such as dibenzoyltartaric acid may also be used. Other suitable resolving acids include (+)-mandelic acid and (+)-5-acetoxy-4-methylpentanoic acid.

By selecting the right conditions a D-isomer may be prepared from the corresponding L-isomer, the racemic mixture, or any other mixture of D- and L-isomers. Furthermore by selecting the right conditions an L-isomer may be prepared from either the corresponding D-isomer or a mixture of D- and L-isomers. The starting material may be the "wrong" isomer or a mixture of isomers in the form of a salt with the resolving acid. All such processes are included within the scope of the present invention.

Furthermore the ester may be used in the form of a Schiff base with the selected aldehyde or ketone. Thus, for example, it may be convenient to start with the preformed α-amino acid ester hemitartrate; these salts may be prepared from the crude esters.

Alternatively, the Schiff base from the α-amino acid ester and an aldehyde or ketone can be formed in solution in a solvent such as benzene, with removal of the water azeotropically or using a drying agent such as magnesium sulphate. This racemic Schiff base may then be reacted with a resolving acid such as tartaric acid in a suitable solvent to give the desired enantiomer.

Where an ester of an α-amino acid of formula I is used in which $R^1$ represents an aryl group (as hereinbefore defined), it is preferred to produce the D-isomer; the L-isomer may be produced in a similar way and may also find utility in the synthesis of antibiotics. Similarly, naturally occuring α-amino acids will usually be required in the L- form but nevertheless it may be useful to obtain the D- form for organic synthesis, e.g. in the preparation of analogues of the above-described cephalosporin and penicillin antibiotics.

In particularly preferred embodiments of the invention, certain combinations of DL-esters, resolving acid, carbonyl reagents and solvents have given especially good results in terms of yield and optical purity of the product.

Using DL-phenylglycinate esters with (+)-tartaric acid to obtain D-phenylglycine ester (+)-hemitartrates, we have found that the methyl ester gives best results using benzaldehyde or acetone in ethanol as solvent. The ethyl ester gives best results using benzaldehyde in methanol or, still better, ethanol as solvent or using acetone in ethanol or methanol as solvent.

Using DL-p-hydroxyphenylglycinate esters with (+)-tartaric acid to obtain D-p-hydroxyphenylglycinate ester (+)-hemitartrates, we found that the methyl ester gives best results using benzaldehyde in acetontrile or, still better, methanol/benzene as solvent. The ratio of methanol:benzene has some effect on the result and a ratio of about 4:1 is preferred. The ethyl ester gives best results with acetone in methanol as solvent or with benzaldehyde in methanol/methylene chloride as solvent. The ratio of methanol:dichloromethane is preferably about 1:1.

When an aldehyde is used in the process of our invention it may be desirable to exclude air (or oxygen) from the reaction mixture, in order to avoid oxidation of the aldehyde to the corresponding acid.

As already indicated the process of our invention is conveniently effected in the presence of a solvent other than the aldehyde or ketone although an excess of the aldehyde or ketone may serve as solvent in some cases. Any total solvent system from which the desired isomer preferentially comes out of solution may be suitable. It is advantageous to determine the preferred solvent system by appropriate preliminary "trial and error" experimentation. As indicated above, methanol, ethanol and acetonitrile as single solvents and methanol/benzene and methanol/methylene chloride as mixed solvents find particular application in the process of the invention. Other solvents which may be used include ethylene glycol, digol, isopropanol, diglyme, tetrahydrofuran containing for example about 10% water, ethanol containing up to 10% water, methanol/1,2-dichloroethane, butane-1,3-diol/methylene chloride, dimethylacetamide/methylene chloride and hexamethyl phosphoramide/methylene chloride.

As stated above esters of p-hydroxyphenylglycine are preferred compounds for use in the process of the present invention and particularly preferred solvent systems for these esters, when the desired product is the D-isomer, include acetonitrile (as single solvent) and methanol, which is preferably in combination with a solvent which reduces the solubility of the hemitartrate, e.g. a chlorinated hydrocarbon such as 1,2-dichloroethane or methylene chloride or an aromatic hydrocarbon, preferably benzene. When the desired product is the L-isomer, preferred solvents with methanol include acetonitrile, carbon tetrachloride and ethyl acetate.

It is believed that the preferential crystallisation of the "right" isomer may be solvate dependent and the preferred solvates for certain given systems are exemplified in the present specification. It will be appreciated that the preferred solvate may differ from one ester to another and thus the yield of the "right" (i.e. the desired optically active isomer) isomer may be increased by choosing the most appropriate solvent. As stated above it is consequently advantageous to determine the most appropriate solvent for any particular case by preliminary "trial and error" experimentation.

The concentration of the ester may be relatively high and, for example, in methanol/acetone 1:1, the ethyl ester of DL-p-phydroxyphenylglycine was resolved in substantially higher yield at a concentration of 13.7% than at 10%. In methanol:benzene (55:45), the concentration is preferably about 5% whereas in methanol:benzene (2:1) it is preferably about 8%.

In general, the concentration of ester in the reaction mixture may be up to 50% and as low as 0.7% but is preferably between 2.0 and 30% depending on solubilities of the various components.

It has been found advantageous to re-use the filtrate from one treatment as the solvent for the next. Thus by repeatedly re-using the filtrate from one treatment as the solvent for the next treatment improved overall yield of the desired enantiomer and good economy in respect of the particular aldehyde or ketone used may, in general, be achieved. This recycling process may, for example, be effected up to at least twelve times.

The process of our invention may conveniently be initiated at temperatures up to about 80°C. In general the whole process may conveniently be effected at ambient temperature or the process initiated at ambient temperature and the mixture cooled to a temperature as low as −30°C. It is preferred to stir the mixtures. It is useful to seed the reaction mixture with the desired product.

The yield of product, in general, increases with time. Thus, for example at room temperature, for the methyl or ethyl esters of phenylglycine and p-hydroxyphenylglycine best results usually attend reaction times of about ½–3 days, e.g. 20–24 hours, but can be as low as 6–8 hours. In general the choice of reaction conditions will follow from experiments involving isolation of the precipitate and measurement of its optical purity by rotation and its chemical purity by thin layer chromatography or spectroscopic means.

In general, where esters of formula II are used in which $R^1$ is other than aryl, longer reaction times are necessary, since in this case reacmisation is usually slower, and reaction times of more than two days may well be required.

Where the reaction is carried out for a relatively long time using an alcohol solvent different from that used to esterify the α-amino acid, some ester exchange may take place; we have found however that the mixed esters are optically pure, that is, they are esters of the same optical isomer of the α-amino acid.

While we do not wish to be bound by theoretical considerations, it is believed, from deuteration experiments on the methyl and ethyl esters of phenylglycine with benzaldehyde and dimethyl sulphoxide or methanol, that the racemisation proceeds via the charged species:

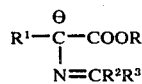

This charged species may, however, only be present in low concentration.

The conversion of the salts of the optically active α-amino acid esters into optically active α-amino acids may be carried out by first removing the optically active acid e.g. (+)-tartaric acid, e.g. on a basic ion exchange column or by formation of an insoluble salt, e.g. the tartrate, e.g. by addition of ammonia in an organic solvent such as ethanol and hydrolysing the free optically active α-amino acid ester. Alternatively the free optically active α-amino acid ester may be obtained by neutralising the optically active salt with a base, e.g. aqueous ammonium hydroxide, sodium hydroxide or sodium bicarbonate to ca. pH7 and extracting with an organic solvent or by precipitating the ester. Care must be exercised in releasing the free optically active α-amino acid ester especially a 2-amino-2-arylacetic ester since it may racemise, especially on warming or in the presence of weak acid or weak base.

Because of the risk of racemisation we have found it advantageous simply to hydrolyse directly the salt of the optically active ester (i.e. one avoids releasing the free optically active amino ester). Alternatively the salt may be converted into another salt before hydrolysis e.g. by addition of a calcium salt e.g. calcium chloride. When the process is operated in any of these ways no or very little racemisation occurs, and the α-amino acid of good optical purity can be obtained.

Free amino acids, may be obtained by hydrolysing the obtained ester, preferably using a salt as indicated above, in an aqueous solution of a strong acid e.g. having a pH of 2.5 or less, preferably 1.5 or less such as a mineral acid or an alkane- or arylsulphonic acid or a halogenated carboxylic acid, e.g. hydrochloric, hydrobromic, hydriodic, sulphuric, phosphoric, perchloric, trifluoroacetic, methanesulphonic or p-toluene sulphonic acid.

In order to achieve optimum hydrolysis it is advantageous to use at least 2.5 equivalents, preferably at least 3–4 equivalents of acid.

The hydrolysis reaction may be carried out at 20° to 150°C and is conveniently effected at the boiling point of the aqueous acid solution. It has been found that even at the boiling point little or no racemisation occurs. It is most important that strong acid hydrolysis be used.

The product of the acid hydrolysis is a solution containing a salt of the optically active amino acid. The optically active amino acid may be liberated by adjusting the pH of the hydrolysis mixture with a base to the isoelectric point of the amino acid and filtering or extracting as required. Alternatively ion exchange processes may be used.

The optically active α-amino acid esters or their salts may also be converted into their corresponding optically active α-amino acids in good yield by the use of a base i.e. a strong base having, for example, a pH greater than 10 preferably greater than 10.5, advantageously greater than 12. This is particularly surprising since the use of a base in the hydrolysis of an optically active 2-amino-2-arylacetic acid ester has been reported to lead to racemisation.

The basic conditions may be achieved by addition of a strong inorganic base capable of generating a sufficiently high pH e.g. an alkali metal hydroxide such as sodium or potassium hydroxide or an alkaline earth metal hydroxide such as barium hydroxide, ammonium hydroxide and water soluble strong organic bases may also be used. It is generally necessary to use at least 1.0 equivalent, but preferably 1–2 equivalents of sodium hydroxide or other equivalent bases together where hydrolysis is effected directly on the salt with sufficient additional base to liberate the amino acid ester from its salt.

In a single stage process under basic conditions using a hemitartrate salt, at least 3 equivalents, but preferably 3 to 4 equivalents, of base are required.

The base hydrolysis is preferably effected at temperatures of e.g.. from the freezing point of the mixture to 60°C, more preferably 20° to 40°C, conveniently for a short period of time e.g. about 15 minutes. Reaction times of 1 minute to 24 hours have, however, been used. The optimal time and temperature can be determined by a preliminary study.

The conversion of the salts of optically active esters of phenylglycine and p-hydroxyphenylglycine into their corresponding optically active acids is preferably effected by base hydrolysis.

The optically active resolving agent e.g. (+)-tartaric acid, may be recovered from the mother liquors by conventional techniques and recycled.

According to a further feature of the present invention there are provided esters of the formula:

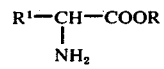

(wherein R is as hereinbefore defined and $R^1$ represents a substituted or unsubstituted aryl group other than an unsubstituted phenyl group) in substantially optically pure form.

Preferred esters according to the present invention include:
methyl D-m-methoxyphenylglycinate in substantially optically pure form;
methyl D-p-chlorophenylglycinate in substantially optically pure form;
methyl D-p-hydroxyphenylglycinate in substantially optically pure form; and
ethyl D-p-hydroxyphenylglycinate in substantially optically pure form.

According to a still further feature of the present invention there are provided (+)-hemitartrate salts of esters of the formula:

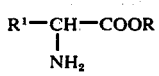

(wherein R is as hereinbefore defined and $R^1$ is a substituted or unsubstituted aryl group other than unsubstituted phenyl) and solvates thereof. The hemitartrate salts are preferably in substantially optically pure form. Hemitartrate salts include, for example, the following:
methyl D-m-methoxyphenylglycinate (+)-hemitartrate and its methanol solvate;
methyl D-p-chlorophenylglycinate (+)-hemitartrate and its methanol solvate;
methyl D-p-hydroxyphenylglycinate (+)-hemitartrate and its solvates with methanol, acetonitrile and benzene;
ethyl D-p-hydroxyphenylglycinate (+)-hemitartrate and its methanol solvate;
methyl D-2-thienylglycinate (+)-hemitartrate.

A further useful solvate is ethyl D-phenylglycinate (+)-hemitartrate monomethanol solvate.

According to a yet still further feature of the present invention there are provided Schiff bases of esters of the formula:

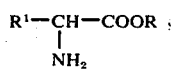

[wherein R is as hereinbefore defined and $R^1$ represents aryl (including phenyl)].

Schiff bases according to the present invention thus include, for example, N-benzylidene methyl and ethyl DL-phenyl glycinates and N-benzylidene, N(p-nitrobenzylidene) and N(-p-methoxybenzylidene) methyl DL-p-hydroxyphenyl glycinates.

The following non-limiting examples illustrate the invention.

In these Examples, we define optical purity as a percentage taking a racemic mixture as having an optical purity of 0%. The yields given are percentages independent of the amount of the desired optical isomer in the starting material. This definition for example can give a yield of 100% in a complete resolution where all the unwanted isomer in a racemic starting material has been converted to the desired isomer. The rotations and percentage yields given are values calculated to the unsolvated material.

Temperatures are in degrees centigrade. Melting points were determined on the Kofler melting point apparatus using approximately 0.05 mg. of sample and a heating ratio of between 1° and 2°/min. The polarised filter was useful to detect the end of the melting range. Some hemitartrate solvates melted over a range of ca 20°. This was possibly due to loss of solvent.

EXAMPLE 1

Resolution with Racemisation of Methyl DL-Phenylglycinate using Benzaldehyde

A solution of methyl DL-phenylglycinate (4.86 g., 29.5 mmole) and (+)-tartaric acid (4.9 g., 32.6 mmole, 1.1 equiv.) in ethanol containing benzaldehyde (51 ml., containing 3.16 ml. PhCHO, 1.05 equiv.) at about 70° was stirred. A solid crystallised almost immediately. The mixture cooled to about 25° during 30 minutes, and was stirred at about 25° for 5 days.

The solid was filtered off, then washed with solvent (10 ml.), displacement washed with solvent (10 ml.), and washed with ethanol (10 ml.). It was dried at 28°/3 mm. for 4 hours to give methyl D-phenylglycinate (+)-hemitartrate (9.46 g., 89%), as a monoethanol solvate, m.p. 142° to 144°, $[\alpha]^{25}_d$ −63° (c 2.5, $H_2O$).

EXAMPLE 2

Following the general procedure of Example 1, but using different aldehydes to form the Schiff base, D-phenylglycinate (+)-hemitartrate esters were prepared as set out in Table A.

TABLE A

Resolution with Racemisation of Esters of DL-Phenylglycine in Ethanol with Various Aldehydes.

| Aldehyde | Equivs. Aldehyde | Ester | Conc. Ester % w/v | Time Hrs. | Temp.° | $[\alpha]_D°$ | % Optical Purity | Yield % |
|---|---|---|---|---|---|---|---|---|
| MeO-C₆H₄-CHO | 1 | Et | 10 | 19 | 20 | −46 | 95 | 76 |
| NO₂-C₆H₄-CHO | 1 | Et | 10 | 19 | 20 | −46 | 95 | 51 |
| C₆H₅-CHO | 1 | Et | 10 | 18 | 20 | −46 | 95 | 73 |
| $CH_3CHO$ | 1 | Et | 10 | 19 | 20 | −44.5 | 93 | 68.5 |
| $CH_2O$ | 1 | Et | 10 | 42 | 20–26 | −46 | 95 | 38.5 |
| PhCHO | 1 | Et + Me = 57:43 | 20 | 70 | 20–25 | −53.5 | 96 | 82.5 |
| PhCHO | 1 | Et + Me = 55:45 | 10 | 24 | 20 | −52 | 94 | 59 |

EXAMPLE 3

Resolution with Racemisation of Methyl DL-phenylglycinate using Acetone

Methyl DL-phenylglycinate (4.98 g., 30.2 mmole), (+)-tartaric acid (4.54 g., 30.2 mmole, 1 equiv.) and acetone (4.5 ml., 61.2 mmole, 2 equiv.) were stirred in dry ethanol (46 ml.) at 20° to 25° for 44 hours. The mixture was filtered and the solid washed with ethanol (2 × 15 ml.) and dried at 27°/3 mm. for 2½ hours to give methyl D-phenylglycinate (+)-hemitartrate as a mono-ethanol solvate, (9.93 g., 91%), $[\alpha]_D^{23}$ −63.5° (c 2.5, $H_2O$).

EXAMPLE 4

Following the general procedure of Example 3 but using various ketones to form the Schiff base, D-phenylglycinate (+)-hemitartrate esters were prepared as set out in Table B.

TABLE B

Resolution with Racemisation of Esters of DL-Phenylglycine in Ethanol in the Presence of Ketones

| Ketone | Equivs. of Ketone | Ester | Conc. of Ester % w/v | Time of Stirring | Temp.° | $[\alpha]_D°$ | % Optical Purity | Yield % |
|---|---|---|---|---|---|---|---|---|
| $Me_2CO$ | 2 | Et | 10 | 165 hours | 20–25 | −46.5 | 96 | 89.5 |
| $Me_2CO$ | 2 | Me | 10 | 44 hours | 20–25 | −63.5 | 98 | 91 |
| $Me_2CO$ | 2 | Me | 8 | 142 hours | 20–25 | −63 | 98 | 90.5 |
| Me(Et)CO | 2 | Me | 10 | 122 hours | 20–25 | −64.5 | 99 | 92 |

TABLE B-continued

Resolution with Racemisation of Esters of DL-Phenylglycine in Ethanol in the Presence of Ketones

| Ketone | Equivs. of Ketone | Ester | Conc. of Ester % w/v | Time of Stirring | Temp.° | $[\alpha]_D°$ | Product - hemitartrate | |
|---|---|---|---|---|---|---|---|---|
| | | | | | | | % Optical Purity | Yield % |
| Me\C=O/CH₂CHMe₂ | 2 | Me | 10 | 140 hours | 20–25 | −63 | 97 | 96 |
| (cyclopentanone) | 2 | Me | 10 | 141 hours | 20–25 | −63 | 97 | 92.5 |
| (cyclohexanone) | 2 | Me | 10 | 141 hours | 20–25 | −65 | 100 | 94.5 |
| PhCOMe | 2 | Me | 10 | 288 hours | 20–25 | −61.5 | 95 | 94.5 |

EXAMPLE 5

Resolution with Racemisation of Ethyl DL-Phenylglycinate using Benzaldehyde in Ethanol Solutions of ethyl DL-phenylglycinate (5.0 g., 27.95 mmole), (+)-tartaric acid (4.417 g., 29.45 mmole, 1.05 equiv.), and benzaldehyde (2.85 ml., 27.95 mmole, 1.0 equiv.) in ethanol (total volume 47 ml.) were mixed at 58°. The solution was cooled to 20° to 26° and stirred for 24 hours to give a white solid which was washed with ethanol (2 × 10 ml.), and dried at 29°/2 mm. for 6 hours to give ethyl D-phenylglycinate (+)-hemitartrate as a mono-ethanol solvate (7.95 g., 76%), $[\alpha]_D^{20}$ −47° (c 2.5, H₂O).

EXAMPLE 6

Resolution with Racemisation of Ethyl DL-Phenylglycinate using Benzaldehyde in Methanol A solution of ethyl DL-phenylglycinate (6.26 g., 35 mmole) and (+)-tartaric acid (5.56 g., 1.05 equiv.) in dry methanol containing benzaldehyde (7% v/v benzaldehyde, 1 equiv; total volume 46 ml.) at 50° was cooled from 50° to 22° and stirred for 25 hours. The solid was filtered off and washed with methanol containing 7% benzaldehyde (15 ml.) then methanol (10 ml.) and dried at 22°/2 mm. for 3 hours to give ethyl D-phenylglycinate (+)-hemitartrate as a mono-methanol solvate (5.50 g., 43%), m.p. 131°–135° $[\alpha]_D^{24}$ − 48° (c 2.68, H₂O).

The filtrate was cooled to 0°, then stirred while cooling to −30° for 24 hours to give a second crop (2.09 g., 16%) $[\alpha_D^{23} - 48°$, (c 2.45, H₂O).

EXAMPLE 7

Resolution with Racemisation of Ethyl DL-Phenylglycinate using Acetone in Ethanol A solution of ethyl DL-phenylglycinate (5.00 g., 28 mmole) and (+)-tartaric acid (4.18 g., 28 mmole, 1 equiv.) in ethanol (50 ml.) was made at 58°. The solution was cooled, acetone (4.1 ml., 55.6 mmole, 2 equiv.) was added and the mixture was stirred at 20° to 25° for 165 hours. The solid was filtered off, washed with ethanol (2 × 10 ml.) and dried at 26°/2 mm. for 4½ hours to give ethyl D-phenylglycinate (+)-hemitartrate as a monoethanol solvate (9.338 g., 89%), $[\alpha]_D$ −46.5° (c 2.5 H₂O).

EXAMPLE 8

Resolution with Racemisation of Methyl DL-Phenylglycinate (+)-Hemitartrate using Benzaldehyde Methyl DL-phenylglycinate (+)-hemitartrate (8.528 g., 27.1 mmole) was added with stirring to a solution of benzaldehyde (2.8 ml., 1 equiv.) in ethanol (40 ml.). After 44 hours stirring at 20° to 22°, the mixture was filtered, washed with ethanol (12 ml.), displacement washed with ethanol (12 ml.), then dried at 22° for 2½ hours to give the D-hemitartrate as a mono-ethanol solvate (7.632 g., 78%), $[\alpha]_D^{20}$ −61.5° (c 2.5, H₂O).

EXAMPLE 9

Optical Inversion of Ethyl L-Phenylglycinate (+)-Hemitartrate

A solution of ethyl L-phenylglycinate (+)-hemitartrate (9.45 g., 28.1 mmole, $[\alpha]_D$ + 61°) and benzaldehyde (2.85 ml., 28.1 mmole, 1 equiv.) in ethanol (47 ml.) at 50° was cooled at 25°. After 50 minutes crystallisation began and the mixture was stirred at 20° to 25° for 47 hours. The solid was filtered off, washed with ethanol (2 × 8 ml.) and dried at 20°/2 mm. for 3 hours to give ethyl D-phenylglycinate (+)-hemitartrate as a mono-ethanol solvate (7.50 g. 71%), $[\alpha]_D^{22}$ −47° (c 2.5, H₂O).

EXAMPLE 10 a. N-Benzylidene Ethyl DL-Phenylglycinate

A solution of benzaldehyde (1.07 g., 10.1 mmole) and ethyl phenylglycinate (1.785 g., containing 12% w/w dichloroethane, 8.8 mmole) was stirred in ethanol (10 ml.) for 24 hours at 20° to 25°. The solution was rotary evaporated at 40°/20 mm. and dried by refluxing in benzene in a Dean & Stark apparatus for 2 hours. The solution was evaporated to give the crude Schiff base as an oil 2.7 g., 100%) contaminated with 15% benzaldehyde.

b. Ethyl D-Phenylglycinate (+)-Hemitartrate from N-Benzylidene Ethyl DL-Phenylglycinate A solution of N-benzylidene ethyl DL-phenylglycinate (1.63 g., 6.1 mmole) and (+)-tartaric acid (1.08 g., 7.2 mmole, 1.15 equiv.) in ethanol (15 ml.) was cooled from 60° to 25° and stirred at 20° to 25° for 41 hours. The solid was filtered off, washed with ethanol (2 × 3 ml.), and dried at 20°/2 mm. for 2 hours to give ethyl D-phenylglycinate (+)-hemitartrate containing 0.8 mole of ethanol (1.34 g., 60%), $[\alpha]_D^{20} -48°$ (c 2.56, $H_2O$).

EXAMPLE 11

Resolution with Racemisation of Isopropyl DL-Phenylglycinate

A solution of isopropyl DL-phenylglycinate (3.551 g., 18.3 mmole) and (+)-tartaric acid (2.858 g., 19.0 mmole, 1.04 equiv.) in ethanol (36 ml.) was stirred with benzaldehyde (1.0 ml., 1.05 g., 10 mmole, 0.55 equiv.). A solid rapidly crystallised and the mixture was stirred at 20° to 25° for 6 days, and then filtered. The product was washed with ethanol (2 × 10 ml.) and dried at 20°/2 mm. for 2 hours giving isopropyl L-phenylglycinate (+)-hemitartrate solvated with 0.5 mole ethanol (4.125 g., 62%), $[\alpha]_D^{20} + 56.8°$ (c 2.720, $H_2O$) m.p. 119° to give a liquid and a solid. This solid had a melting point of 141°–143° giving a liquid which gave fine needles m.p. 149°–150°. (The solvated salt was dried at 20°/1mm. to give the unsolvated salt m.p. 135°–143° which gave a liquid which gave fine needles m.p. 149°–150°).

EXAMPLE 12

Resolution with Racemisation of Ethyl DL-Phenylglycinate with (−)-Dibenzoyltartaric Acid A solution of ethyl DL-phenylglycinate (5.095 g., contains 2.5% dichloroethane i.e. 27.7 mmole) and (−)-dibenzoyltartaric acid ($[\alpha]_D$ −114.9°, 10.332 g., 28.9 mmole, 1.04 equiv.) in methanol (59 ml.) was stirred. Crystallisation occurred immediately giving a very stiff mixture which soon became more mobile, and benzaldehyde (2.8 ml., 2.93 g., 27.6 mmole, 1 equiv.) was added. After 117 hours, the mixture was filtered and the product was washed with methanol (2 × 10 ml.) and dried at 20°/4 mm. for 5 hours giving ethyl L-phenylglycinate (−)-dibenzoyl hydrogen tartrate (11.340 g., 76%), m.p. 180° to 183°, $[\alpha]_D^{20}$ −65.4° (c 2.009, MeOH).

EXAMPLE 13

Resolution with Racemisation of Pure Methyl DL-Phenylglycinate in Aqueous IMS using Benzaldehyde A solution of pure methyl DL-phenylglycinate (4.674 g., 28.3 mmole) and (+)-tartaric acid (4.285 g., 28.6 mmole, 1.01 equiv.) in 10% aqueous IMS (47 ml.) was seeded with methyl D-phenylglycinate (+)-hemitartrate ($[\alpha]_D$ −64.6°). Crystallisation began immediately. After 2 hours, benzaldehyde (2.9 ml., 3.03 g., 28.5 mmole, 1 equiv.) was added and the mixture was stirred for 48 hours, and then filtered. The product was washed with 10% aqueous IMS (2 × 8 ml.) and dried at 20°/4 mm. for 2½ hours giving methyl D-phenylglycinate (+)-hemitartrate solvated with 1.0 mole ethanol (7.38 g., 72%), $[\alpha]_D^{20}$ −63.2° (c 2.508, $H_2O$).

EXAMPLE 14

Resolution with Racemisation of Pure Methyl DL-Phenylglycinate in Aqueous IMS using Acetone.

Similarly to Example 13 but using methyl DL-phenylglycinate (4.818 g., 29.2 mmole) and (+)-tartaric acid (4.449 g., 29.9 mole, 1.02 equiv.) in 10% aqueous IMS (48 ml.) and adding acetone (4.3 ml., 3.40 g., 58.5 mmole, 2 equiv.) instead of benzaldehyde to give methyl D-phenylglycinate (+)-hemitartrate solvated with 1.0 mole ethanol (5.195 g., 49%), $[\alpha]_D^{20}$ −63.1° (c 2.495, $H_2O$).

EXAMPLE 15

Resolution with Racemisation of Methyl DL-Phenylglycinate in Ethanol/Acetone A solution of methyl DL-phenylglycinate (4.984 g., —contains 1.5% methylene chloride i.e. 29.7 mmole) in ethanol/acetone was added to a stirred solution of (+)-tartaric acid (4.463g., 29.8 mmole, 1.00 equiv.) in ethanol/acetone [total volume 50 ml., containing 36% v/v acetone (8.2 equiv.)] over 2 hours. No crystallisation had occurred after 20 minutes when ca. half the ester had been added. The solution was seeded with methyl D-phenylglycinate (+)-hemitartrate ($[\alpha]_D$ −64.6°) and crystallisation began immediately. The mixture was stirred for 20 hours and filtered. The product was washed with ethanol/acetone (2 × 15 ml.) and dried at 20°/3 mm. for 3 hours giving methyl D-phenylglycinate (+)-hemitartrate solvated with 1.0 mole ethanol (9.963 g., 93%), $[\alpha]_D^{21}$ − 64.4° (c 2.483, $H_2O$).

EXAMPLE 16

Resolution with Racemisation of Methyl DL-Phenylglycinate using (−)-Tartaric Acid A solution of methyl DL-phenylglycinate (21.961 g., − contains 1.5% methylene chloride i.e. 0.131 mole) in ethanol/acetone was added to a stirred solution of (−)-tartaric acid (19.657 g., 0.131 mole, 1.00 equiv.) in ethanol/acetone [total volume 220 ml. containing 35% v/v acetone (8 equiv.)] over 2 hours. Crystallisation began within 5 minutes giving a granular precipitate. The mixture was stirred for 115 hours, filtered, and the product was washed with solvent (2 × 55 ml.), and dried at 20°/4 mm. for 5½ hours giving methyl L-phenylglycinate (−)-hemitartrate solvated with 1.0 mole ethanol (43.8 g., 93%), m.p. 139° to 145°, $[\alpha]_D^{21}$ + 62.8° (c 2.508, $H_2O$), $[\alpha]_D^{24}$ + 61.9° (c 2.494, $H_2O$).

The product (5.133 g.,) was recrystallised twice from 10% aqueous IMS giving methyl L-phenylglycinate (−)-hemitartrate mono-ethanol solvate, $[\alpha]_D^{23}$ + 63.9° (c 2.509, $H_2O$) and $[\alpha]_D^{24}$ + 64.0° (c 2.500, $H_2O$).

EXAMPLE 17

Resolution with Racemisation of Ethyl DL-Phenylglycinate using (+)-Tartaric Acid (0.5 equiv.)

A mixture of ethyl DL-phenylglycinate (5.021 g., 96% pure i.e. 27.0 mmole) and (+)-tartaric acid (2.027 g., 13.5 mmole, 0.5 equiv.) in ethanol (47 ml.) and benzaldehyde (2.75 ml., 2.88 g., 27.1 mmole, 1 equiv.) was stirred at 20°; crystallisation began within 5 minutes. After 10 days the mixture was filtered and the product washed with ethanol (2 × 7 ml.) and dried at 20°/4 mm. for 3 hours giving ethyl D-phenylglycinate (+)-hemitartrate solvated with 1.0 mole ethanol (3.922 g., 39% yield based on ester present or 78% yield based on (+)-tartaric acid present), $[\alpha]_D^{21}$ − 45.9° (c 2.506, $H_2O$).

EXAMPLE 18

Resolution with Racemisation of Ethyl DL-Phenylglycinate in Methanol/Acetone

A solution of ethyl DL-phenylglycinate (5.051 g., contains 0.05 mole methylene chloride i.e. 27.5 mmole) and (+)-tartaric acid (4.264 g., 28.4 mmole, 1.03 equiv.) in methanol: acetone (1:1, 50 ml.) was stirred at 20° to 25°; crystallisation began immediately. After 23½ hours the mixture was filtered and the product washed with solvent (2 × 12 ml.) and dried at 24°/2 mm. for 3½ hours giving ethyl D-phenylglycinate (+)-hemitartrate solvated with 1.0 mole methanol (7.265g., 73%), $[\alpha]_D^{24} - 47.4°$ (c 2.519, $H_2O$).

Example 19

Resolution with Racemisation of Ethyl DL-Phenylglycinate in Methanol/Acetone — Re-use of Filtrate Similarly to Example 18 but using ethyl DL-phenylglycinate (5.070 g., — contains 0.05 mole methylene chloride i.e. 27.6 mmole) and (+)-tartaric acid (4.275 g., 28.5 mmole, 1.03 equiv.) in the filtrate from a previous resolution (Example 18, 50 ml. — made up to volume with the first and then second washes), and giving ethyl D-phenylglycinate (+)-hemitartrate solvated with 1.0 mole methanol (8.049 g., 81%), $[\alpha]_D^{23} - 46.7°$ (c 2.520, $H_2O$).

EXAMPLE 20 a. Ethyl DL-p-Hydroxyphenylglycinate

A solution of DL-p-hydroxyphenylglycine (29.74 g., 0.178 mole) was refluxed for 2½ hours in absolute ethanol (150 ml.) with concentrated sulphuric acid (24 ml., 44.2 g., 0.45 mole). The orange solution was cooled and neutralised (pH 7) with ammonium hydroxide solution (0.880; 30 ml.), giving a white solid (ammonium sulphate) which was filtered off and washed with ethanol. The filtrate was evaporated to a wet cream solid which was stirred with water at pH 8, filtered, and dried to give the DL-ester as white needles (30.53 g., 88%), m.p. 145° to 155°.

b. Resolution with racemisation of Ethyl DL-p-Hydroxyphenylglycinate using Methanol:Acetone = 1:1

A solution of ethyl DL-p-hydroxyphenylglycinate (8.235 g., 42 mmole) and (+)-tartaric acid (6.425 g., 43 mmole, 1.02 equiv.) in methanol:acetone [made from methanol (30 ml.), which had been distilled from magnesium, and Analar acetone (30 ml.)] was cooled from 50° to 30°, seeded with the D-hemitartrate ($[\alpha]_D - 49.6°$), and stirred. After 5 minutes crystallisation was well established. The mixture was stirred for 40 hours at 23° to 25°, filtered, washed (1 × 12 ml., 1 × 9 ml.), and dried at 20°/2mm. to give ethyl D-p-hydroxyphenylglycinate (+)-hemitartrate as a mono-methanol solvate (10.610 g., 66%), m.p. 88° to 90° (decomp. to give flat needles m.p. 148° to 150°), $[\alpha]_D^{23} - 49.6°$ (c 1.02, $H_2O$).

EXAMPLE 21

Resolution with Racemisation of Ethyl DL-p-Hydroxyphenylglycinate (+)-Hemitartrate A solution of the hemitartrate (1.846 g., 5.1 mmole, $[\alpha]_D - 2.5°$) in warm methanol (5 ml.) was stirred with acetone (5 ml.) and seeded with D-hemitartrate (mono-methanol solvate, $[\alpha]_D - 49.8°$). The mixture was stirred at 20° to 25° for 14 days, was filtered, washed (3 × 2 ml.), and dried at 20°/2 mm. for 3 hours to give the hemitartrate solvated with 0.5 mole methanol (1.258 g., 68%), $[\alpha]_D^{22} - 48.3°$ (c 1.022, $H_2O$).

EXAMPLE 22

Resolution with Racemisation of Ethyl DL-p-Hydroxyphenylglycinate — Re-using the Filtrate of a Previous Resolution A cloudy solution of the ester (5.289 g., 27 mmole) and (+)-tartaric acid (4.05 g., 27 mmole, 1 equiv.) in the filtrate from a previous resolution (50 ml.) was cooled from 50 to 40° and seeded with D-hemitartrate (mono-methanol solvate, $[\alpha]_D - 49.6°$). At 30° (after 5 minutes) a meniscus of solid had appeared and crystallisation was complete after a further 5 minutes. The straw coloured mixture was stirred at 7° to 23° for 67 hours and was filtered (tan liquid, 43 ml.), washed (1 × 10 ml., 1 × 8 ml.), and dried at 23°/2 mm. for 2 hours to give the D-hemitartrate as needles of the monomethanol solvate (6.43 g., 64%), m.p. 88° to 90° (decomp. to give a liquid, then flat needles m.p. 148° to 150°, possibly the unsolvated salt), $[\alpha]_D^{23} - 50.5°$ (c 1.078, $H_2O$).

A portion (1.904 g.) of the solvated salt was dried at 70°/2 mm. for 8 hours to give a product (1.782 g., 6.4% weight loss; 8.5% calculated for 1.0 $CH_3OH$) containing 0.3M methanol, $[\alpha]_D^{20} - 49.1°$ (c 1.37, $H_2O$).

Another sample (2.5558 g.) was dried at 90° for 17 hours to give the salt as the hemihydrate (2.3120 g.), m.p. 148° to 151°, $[\alpha]_D^{26} - 49.2°$ (c 1.032, $H_2O$).

EXAMPLE 23

Methyl DL-p-Hydroxyphenylglycinate

A solution of DL-p-hydroxyphenylglycine (4.96 g., 29.6 mmole) and concentrated sulphuric acid (3.95 ml., 7.26 g., 74.1 mmole) in dried methanol (20 ml.) was refluxed for 2 hours. Ammonium hydroxide solution (0.880, 6 ml.) was added to neutralise the solution (pH 7), giving a solid which was washed with methanol, then water, and was dried at 100°/2 mm. for 2 hours to give the DL-ester (4.80 g., 89.5%) as needles, m.p. 178° to 180°.

EXAMPLE 24

N-Benzylidene Methyl DL-p-Hydroxyphenylglycinate

A suspension of methyl DL-p-hydroxyphenylglycinate (insoluble in benzene, 0.206 g. 1.14 mmole) and benzaldehyde (0.121 g., 1.14 mmole, 1 equiv.) in benzene (16 ml.) was refluxed for 5½ hours using a Dean and Stark apparatus. Insoluble material was filtered off and the filtrate was concentrated. The solid which crystallised was filtered, washed with benzene (2 × 1 ml.), and dried at 20°/2 mm. giving the DL-Schiff base (211 mg., 62%), m.p. 129° to 133°.

EXAMPLE 25

N-(p-Nitrobenzylidene) Methyl DL-p-Hydroxyphenylglycinate

Similarly to Example 24 but using methyl DL-p-hydroxyphenylglycinate (0.204 g., 1.13 mmole) and p-nitrobenzaldehyde (0.170 g., 1.12 mmole, 1 equiv.) and giving the DL-Schiff base (134 mg., 38%), m.p. 175° to 182°.

EXAMPLE 26

N-(p-Methoxybenzylidene) Methyl DL-p-Hydroxyphenylglycinate

Similarly to Example 24 but using methyl DL-p-hydroxyphenylglycinate (0.203 g., 1.12 mmole) and anisaldehyde (0.153 g., 1.12 mmole, 1 equiv.) and adding methanol to the benzene to assist solubility to give the DL-Schiff base solvated with anisaldehyde (170 mg., 51%), m.p. 96° to 107°, nmr spectroscopy showed the presence of 0.35 mole anisaldehyde.

EXAMPLE 27

Resolution with Racemisation of Methyl DL-p-Hydroxyphenylglycinate using Benzaldehyde in Methanol:Benzene (55:45)

A solution of methyl DL-p-hydroxyphenylglycinate (5.23 g., 29 mmole), (+)-tartaric acid (4.32 g., 29 mmole, 1 equiv.), and benzaldehyde (3.0 ml., 3.08 g., 30 mmole, 1.03 equiv.) in methanol (25 ml.) was seeded with the D-hemitartrate ($[\alpha]_D$ − 50°) and stirred. The mixture was diluted with benzene (45 ml.) and methanol (30 ml.) and stirred. A solid was obtained almost immediately. The mixture was stirred at 23° for 18 hours, filtered, slurry washed (1 × 20 ml. benzene:methanol = 1:1), displacement washed (1 × 20 ml. $C_6H_6$ : MeOH = 1:1), and dried at 23°/4 mm. to give methyl D-p-hydroxyphenylglycinate (+)-hemitartrate as needles m.p. 105° to 121° (8.97 g., 77.5%), solvated with methanol (1.0 mole) and benzene (0.5 mole), $[\alpha]_D^{23}$ − 65.3° (c 1.094, $H_2O$).

EXAMPLE 28

Resolution with Racemisation of Methyl DL-p-Hydroxyphenylglycinate using Benzaldehyde in Dry Acetonitrile Methyl DL-p-hydroxyphenylglycinate (5 g., 27.6 mmole) was added to a stirred suspension of (+)-tartaric acid (4.2 g; 28 mmole) in dry acetonitrile (40 ml.). After 5 minutes benzaldehyde (2.5 ml., 24.7 mmole) was added and the reaction mixture was stirred at ambient temperature for 7 days. The white solid was isolated by filtration, washed with acetonitrile (17 ml.) and dried in vacuo at 40° for 24 hours to give methyl D-p-hydroxyphenylglycinate (+)-hemitartrate mono-acetonitrile solvate (9.9 g., 96.5%), m.p. 102° to 115° $[\alpha]_D$ − 65° (c 1, $H_2O$).

EXAMPLE 29

Recrystallisation of Methyl D-p-Hydroxyphenylglycinate (+)-Hemitartrate Methanol and Benzene Solvate from Dry Methanol A slightly cloudy solution of methyl D-p-hydroxyphenylglycinate (+)-hemitartrate [made as in Example 27, solvated with methanol (1.0 mole) and benzene (0.4 mole), $[\alpha]_D$ − 64.0°; 6.838 g.] in refluxing Analar methanol (68ml., i.e. 10% hemitartrate) was filtered hot and cooled. A solid rapidly crystallised. After 17 hours at 22° the solid was filtered, washed (1 × 30 ml., 1 × 15 ml.), and dried at 22°/0.1 mm. for 4 hours to give methyl D-p-hydroxyphenylglycinate (+)-hemitartrate solvated with methanol (1.0 mole) and benzene (0.4 mole), (3.733 g., 55%) as small needles, m.p. 104° to 125°, $[\alpha]_D^{22}$ − 68.4° (c 1.015, $H_2O$).

In a similar experiment the hemitartrate (4.4 g., solvated with methanol (1.0 mole) and benzene (0.5 mole); $[\alpha]_D$ − 58.2°) was recrystallised from methanol 25 ml.) and water (3.4 ml.) to give the solvated (1.0 mole methanol, 0.5 mole benzene) hemitartrate (2.9 g., 66%), $[\alpha]_D$ − 68.5°.

EXAMPLE 30

Resolution with Racemisation of Ethyl DL-p-Hydroxyphenylglycinate in Methanol:Methylene Chloride (1:1)

A mixture of ethyl DL-p-hydroxyphenylglycinate (5.087 g., 26.2 mmole) and (+)-tartaric acid (3.920 g., 26.1 mmole, 1.0 equiv.) was added with stirring during 1 hour to a solution of benzaldehyde (3.0 ml., 29.6 mmole, 1.14 equiv.) in methanol (30 ml.) and methylene chloride (30 ml.). A solid started to crystallise half-way through the addition. The solution was seeded with the D-hemitartrate ($[\alpha]_D$ − 49.6°, made as in Example 20 (b)) and stirred at 23° for 18 hours. The mixture was filtered, washed (1 × 15 ml., 1 × 10 ml.), and dried at 23°/1 mm. for 4 hours to give the D-hemitartrate as a mono-methanol solvate (5.994 g., 61%) as small needles, m.p. 94° to 120°, giving leaves m.p. 149° to 155°, $[\alpha]_D^{23}$ − 48.9° (c 1.043, $H_2O$).

EXAMPLE 31

Ethyl L-p-Hydroxyphenylglycinate (−)-Hemitartrate

A suspension of ethyl DL-p-hydroxyphenylglycinate (26.65 g., 0.1365 mole) and (−)-tartaric acid (20.8 g., 0.1385 mole) in a mixture of Analar acetone (97.5 ml.) and Analar methanol (97.5 ml.) was stirred and warmed to 49° to give a cloudy solution. This solution was stirred and allowed to cool, seeding with the L-hemitartrate ($[\alpha]_D$ + 46°). The stirring rate was increased as crystallisation took place, and then reduced as the slurry thinned. The mixture was stirred for 48 hours at ca. 25°, filtered, washed with cold acetone-methanol (1:1, 70 ml.), and dried at 20° in vacuo to give ethyl L-p-hydroxyphenylglycinate (−)-hemitartrate as a methanol (0.3 mole) solvate (27.80 g., 58%), $[\alpha]_D^{25}$ + 47.4° (c 1.275, $H_2O$).

EXAMPLE 32

Resolution with Racemisation of Methyl DL-p-Hydroxyphenylglycinate using Methanol:Acetonitrile Analar Laboratory Reagent grade Methanol (30 ml.) and acetonitrile (Analar Laboratory Reagent grade 30 ml.) were stirred at 20° with benzaldehyde (2.82 ml., 2.95 g., 27.8 mmole, 1 equiv.). A mixture of methyl DL-p-hydroxyphenylglycinate (5.037 g., 27.8 mmole, 1 equiv.) and (+)-tartaric acid (4.241 g., 28.3 mmole, 1.02 equiv.) was added gradually so that the mixture remained stirrable. The time for the addition was ca. 2 hours. The mixture was stirred for 17 hours after all the solids had been added. The product was filtered, washed with solvent (2 × 7 ml.), and dried at 20°/2mm. for 2½ hours giving methyl L-p-hydroxyphenylglycinate (+)-hemitartrate mono-methanol solvate (5.642 g., 56%), m.p. 97 to 118°, $[\alpha]_D^{21}$ + 94.5° (c 1. 028, $H_2O$).

EXAMPLE 33

Resolution with Racemisation of Methyl m-Methoxyphenylglycinate

A solution of (+)-tartaric acid (0.804 g., 5.35 mmole, 1.05 equiv.) was added to a solution of methyl DL-m- methoxyphenylglycinate (0.994 g., 5.09 mmole) in dry methanol (total volume 5 ml.) at 20°. Crystallisation began immediately and acetone (5 ml.) was added, with stirring, during 40 minutes. The mixture was stirred at 20° to 25° for 9 days, and was filtered. The product was washed with methanol:acetone (1:1, 2 × 2 ml.) and dried at 20°/2 mm. for 3 hours to give methyl D-m-methoxyphenylglycinate (+)-hemitartrate solvated with 0.8 mole methanol (1.631 g., 86%) m.p. 157°–158°, $[\alpha]_D^{18} - 62°$ (c 2.49, H$_2$O).

EXAMPLE 34

Resolution with Racemisation of Methyl p-Chlorophenylglycinate

A solution of methyl DL-p-chlorophenylglycinate (0.801 g., 4.01 mmole) and (+)-tartaric acid (0.634 g., 4.2 mmole, 1.05 equiv.) in methanol (4 ml.) was stirred for 2 hours at 18°, by which time a solid had crystallised. Acetone (4 ml.) was added over 20 minutes, and the mixtures was stirred at 18° at 25° for 7 days, when it was filtered. The product was washed with methanol:acetone (1:1, 2 × 1 ml.) and dried at 20°/1 mm. Hg for 2 hours to give methyl D-p-chlorophenylglycinate (+)-hemitartrate (0.897 g., 57% yield) as a methanol(0.65M MeOH 0.2M Me$_2$CO 0.15M EtOH) solvate, m.p. 150° – 156° $[\alpha]_D^{22} - 61°$ (c 2.50, H$_2$O).

EXAMPLE 35

Methyl DL-m-Methoxyphenylglycinate

A solution of DL-m-methoxyphenylglycine (15.01 g., 82.8 mmole) in methanol (60 ml.) containing concentrated sulphuric acid (11 ml., 0.207 mole, 2.5 mole equiv.) was refluxed for two hours. The cooled solution was neutralized to pH 7.0 with ammonium hydroxide (16 ml., 0.880, 0.8 equiv.) filtered and the solid was washed with methanol. The filtrate was evaporated to give a yellow oil (38.6 g.) which was stirred with water (20 ml.) and methylene chloride (30 ml.) as the pH was raised from 6 to 7. The aqueous layer was extracted with methylene chloride which was washed, dried, and evaporated to give the ester as a pale yellow oil (13.5 g., 83.5%).

EXAMPLE 36

Methyl DL-p-Chlorophenylglycinate

A solution of DL-p-chlorophenylglycine (7.495 g., 40.5 mmole) in dry methanol (32 ml.) containing concentrated sulphuric acid (5.5 ml., 0.103 mole, 2.5 mole equiv.) was refluxed for 2 hours. The cooled solution was neutralized to pH7 with ammonium hydroxide (8 ml., 0.880, 0.8 equiv.), filtered, and the solid washed with methanol. The filtrate was evaporated to give a yellow solid (17.7 g.) which was stirred with water (30 ml.) and methylene chloride (40 ml.) as the pH was raised from 6 to 8. The aqueous layer was extracted with methylene chloride which was washed, dried, and evaporated to give the ester as a yellow oil (6.169 g., 76.5%), which crystallised on keeping at 4°, m.p. 43° to 44°.

EXAMPLE 37

Resolution with Racemisation of Methyl DL-p-Chlorophenylglycinate using Anisaldehyde A solution of methyl DL-p-chlorophenylglycinate (0.996 g., 5.00 mmole) and (+)-tartaric acid (0.793 g., 5.29 mmole, 1.06 equiv.) in absolute ethanol (10 ml.) containing anisaldehyde (0.343 g., 2.52 mmole, 0.5 equiv.) and stirred at 23°. Crystallisation began immediately but within 25 minutes the solid had redissolved. Stirring was stopped and the solution was seeded with the L-salt to induce crystallisation. The mixture was stirred at 20° to 25° for 17 days and was filtered. The product was washed with ethanol (2 × 1 ml.) and dried at 20°/3 mm. for 4 hours to give methyl D-p-chlorophenylglycinate (+)-hemitartrate unsolvated (0.801 g., 46%), m.p. 155° to 156°, $[\alpha]_D^{18} - 59.9°$ (c 2.485, H$_2$O).

EXAMPLE 38

Resolution with Racemisation of Methyl DL-p-Chlorophenylglycinate

A mixture of methyl DL-p-chlorophenylglycinate (1.308 g., 6.55 mmole) and (+)-tartaric acid (0.986 g., 6.57 mmole, 1.0 equiv.) in absolute ethanol (12 ml.) containing acetone (0.97 ml., 0.77 g., 13.2 mmole, 2 equiv.) was stirred at 20° to 25° for 70 hours. The product was filtered, washed with ethanol (2 × 2 ml.), and dried at 20°/3 mm. for 2½ hours to give a 1:1 mixture of methyl L-p-chlorophenylglycinate (+)-hemitartrate and bis-(methyl L-p-chlorophenylglycinate) tartrate solvated with 0.3 mole ethanol (1.047 g., 52%), $[\alpha]_D^{23} + 60.0°$ (c 2.486, H$_2$O), τ (D$_3$CSOCD$_3$) showed that the resonance for the tartrate proton, 5.84 τ, was only 70% of the expected value for the hemitartrate and therefore that the bis-ester tartrate was present.

EXAMPLE 39

Methyl DL-2-Thienylglycinate

A solution of DL-2-thienylglycine (4.992 g., 31.7 mmole) in methanol (20 ml.) containing concentrated sulphuric acid (4.3 ml., 7.91 g., 80.8 mmole, 2.55 mole equiv.) was refluxed for 1 hour 35 minutes. The cooled solution was neutralised to pH 7 with 10N-ammonium hydroxide (12 ml., 0.75 equiv.), filtered, and the solid was washed with methanol. The filtrate was evaporated to give a cloudy brown oil (14.899 g.), which was stirred with water (15 ml.) and methylene chloride (25 ml.) as the pH was raised from 5 to 7. The aqueous layer was extracted with methylene chloride, which was washed, dried, and evaporated to give the ester as a yellow oil (4.450 g., 82%).

EXAMPLE 40

Resolution with Racemisation of Methyl DL-2-Thienylglycinate

A solution of methyl DL-2-thienylglycinate (1.232 g., 7.20 mmole) and (+)-tartaric acid (1.091 g., 7.27 mmole, 1.01 equiv.) in ethanol/acetone (1:1, 12 ml.) was stirred at 20° for 7 days. Some solid precipitated immediately but then dissolved in ca. 15 minutes. The orange solution was allowed to stand for an hour, during which little crystallisation occurred, and then stirring was restarted. The product was washed with ethanol/acetone (1:1, 2 ×) and dried at 20°/2 mm. for 5 hours to give methyl D-2-thienylglycinate (+)-hemitartrate (0.947 g., 41%), m.p. 144° to 145°, $[\alpha]_D^{23} - 43.6°$ (c 1.000, H$_2$O). ca. 94% optically pure.

EXAMPLE 41

Ethyl DL-p-Methoxyphenylglycinate

A solution of DL-p-methoxyphenylglycine (21.35 g., 0.118 mole) and concentrated sulphuric acid (16 ml., 29.4 g., 0.300 mole, 2.54 mole equiv.) was refluxed in absolute ethanol for 100 minutes. The solution was neutralised to pH 7 with 0.880 ammonium hydroxide (25 ml.) and filtered. The solid was washed with water to give recovered amino acid (1.62 g., 7.5%). The ethanol-soluble filtrate was evaporated and partitioned between water and methylene chloride at pH 7. The organic layer was washed, dried, and evaporated to give the amino ester (20.09 g., 81%, i.e. 88% yield based on consumed amino acid) as a brown oil.

EXAMPLE 42

Isopropyl DL-p-Methoxyphenylglycinate

The ester was made similarly to the ethyl ester (Example 41) but using isopropanol (50 ml.), concentrated sulphuric acid (3.5 ml., 65.6 mmole), and DL-p-methoxyphenylglycine (4.75 g., 26.2 mmole) to give recovered amino acid (0.92 g.) and isopropyl ester (4.02 g., 90%) as a brown oil.

EXAMPLE 43

Ethyl L-p-Methoxyphenylglycinate (+)-Hemitartrate

A solution of ethyl DL-p-methoxyphenylglycinate (1.993 g., 10.2 mmole) and (+)-tartaric acid (1.576 g., 10.5 mmole, 1.03 equiv.) was stirred in ethanol (20 ml.) containing benzaldehyde (1.0 ml., 1.05 g., 10 mmole, 0.98 equiv.) at 50° and cooled to 20° when it crystallised. The pale yellow mixture was stirred at 20° for 12 days, filtered, washed (1 × 4 ml., 1 × 3 ml. of ethanol), and dried at 20°/2 mm. for 3 hours to give the optically impure L-hemitartrate as a solvate (0.4 mole ethanol, 2.380 g., 69%), m.p. 80° to 85°, $[\alpha]_D^{22} + 51.9°$ (c 1.398, $H_2O$).

EXAMPLE 44

Isopropyl L-p-Methoxyphenylglycinate (+)-Hemitartrate

A solution of isopropyl DL-p-methoxyphenylglycinate (0.666 g., 2.99 mmole) and (+)-tartaric acid (0.465 g., 1.04 equiv.) was stirred in ethanol (6.9 ml.) containing benzaldehyde (0.31 ml., 1.02 equiv.). Crystallisation occurred immediately and the mixture was stirred at 20° for 43 hours. The product was filtered, washed (2 × 1.5 ml. ethanol), and dried at 24°/2 mm. for 3½ hours to give the L-hemitartrate as an ethanol solvate (0.1 mole, 0.580 g., 50%), m.p. 134° to 137°, $[\alpha]_D + 50.5°$ (c 1.023, $H_2O$).

EXAMPLE 45

Resolution with Racemisation of 10% Methyl DL-Methioninate in Methanol using Anisaldehyde.

A solution of methyl DL-methioninate (2.506 g., 15.37 mmole) and (+)-tartaric acid (2.372 g., 15.82 mmole, 1.03 equiv.) and dried methanol (25 ml., i.e. 10% ester concentration) was seeded with methyl L-methioninate (+)-hemitartrate ($[\alpha]_D + 29.6°$). Crystallisation occurred slowly and after 1½ hours at 25°, anisaldehyde (1.86 ml., 2.09 g., 15.35 mmole, 1 equiv., 6.9% v/v) was added, the mixture was stirred at 20° to 25° for 18 days and then filtered. The product was washed with methanol (2 × 3 ml.) and dried at 20°/2 mm. for 4 hours to give methyl L-methioninate (+)-hemitartrate (2.959 g., 61.5%), m.p. 142° to 145°, $[\alpha]_D^{21} + 29.9°$ (c 3.016, $H_2O$).

EXAMPLE 46

Resolution with Racemisation of 10% Methyl DL-Methioninate in Methanol using Benzaldehyde, and Re-use of Filtrate As for Example 45 but adding benzaldehyde (1.56 ml., 1.63 g., 15.36 mmole, 1 equiv.) and stirring for 6 days, to give methyl L-methioninate (+)-hemitartrate (2.209 g., 46%), $[\alpha]_D^{25} + 29.8°$ (c 3.016, $H_2O$).

The filtrate and first wash were combined, and used as described below:

A warm solution of (+)-tartaric acid (912 g., 12.76 mmole, 1.03 equiv.) in the above filtrate was added to methyl DL-methioninate (2.024 g., 12.40 mmole, 1 equiv.) in the filtrate (total volume, 20 ml.). The resulting solution was shaken and seeded with methyl L-methioninate (+)-hemitartrate ($[\alpha]_D + 29.6°$). Crystallisation occurred slowly and after ca. 2 hours at 25° stirring was begun. After 28 days the product was filtered, washed, and dried as for Example 45 to give methyl L-methioninate (+)-hemitartrate (4.129 g., 106%), $[\alpha]_D^{22} + 29.8°$ (c 3.020, $H_2O$). The overall yield was 76%.

EXAMPLE 47

Resolution with Racemisation of 20% Methyl DL-Methioninate in Methanol using Anisaldehyde Similarly to Example 45 but using methyl DL-methioninate (10.033 g., 61.5 mmole) and (+)-tartaric acid (9.506 g., 63.4 mmole, 1.03 equiv.) in dried methanol (50 ml., i.e. 20% ester concentration) and adding anisaldehyde (7.5 ml., 8.43 g., 61.9 mmole, 1 equiv.) and stirring for 44 hours to give methyl L-methioninate (+)-hemitartrate (11.208 g., 58%), $[\alpha]_D^{21} + 28.8°$ (c 3.038, $H_2O$).

EXAMPLE 48

Resolution of Ethyl DL-Phenylalaninate with (−)-Dibenzoyltartaric Acid

A solution of ethyl DL-phenylalaninate (8.755 g., 45.5 mmole) and (−)-dibenzoyltartaric acid (8.145 g., 22.7 mmole) in dry ethanol (62.5 ml., i.e. 14% solution of ester) was cooled from 70° to 40°, seeded with an authentic sample of bis-(ethyl D-phenylalaninate) (−)-dibenzoyltartrate, and was allowed to crystallise at 20° for 24 hours. The product was filtered, washed with ethanol (1 × 15 ml., 1 × 10 ml.), and dried at 20°/2 mm. for 4 hours to give bis-(ethyl D-phenylalaninate) (−)-dibenzoyltartrate solvated with 2.0 mole ethanol (7.685 g., 41%), $[\alpha]_D^{20} - 76.5°$ (c 0.28, EtOH), and $[\alpha]_D^{22} - 75.5°$ (c 0.282, EtOH) — 4 dm. tube.

Part (25 ml.) of the filtrate was evaporated to a white solid (3.51 g., 59%), $[\alpha]_D^{22} - 35°$ (c 10, EtOH). Part of the solid (380 mg.) was refluxed under an atmosphere of nitrogen in acetone for 2 hours, kept at 20° for 3 days, and evaporated to give a brown gum, which was dissolved in ethanol (4 ml.) and crystallised to give a second crop of the tartrate (53 mg., 9%), $[\alpha]_D^{22} - 74.2°$ (c 0.27, EtOH).

EXAMPLE 49

Hydrolysis of Methyl D-Phenylglycinate (+)-Hemitartrate

A solution of methyl D-phenylglycinate (+)-hemitartrate (20.49 g., — containing 0.7 mole ethanol i.e. 59.0 mmole) in 6N-hydrochoric acid (38 ml., 228 mmole, 3.9 equiv.) was refluxed for 1 hour 10 minutes, and then concentrated to remove most of the alcohols. The solution was diluted with water (19 ml.) and the pH adjusted to 7.0 with 0.880 ammonia solution. The mixture was cooled in ice for ca. 30 minutes, filtered, the solid washed with water (2 × 12 ml.) and ethanol (12 ml.), and dried over phosphorus pentoxide in vacuo giving D-phenylglycine (8.06 g., 90%) as cream coloured plates, sublimed 245° – 249°, $[\alpha]_D^{25} - 154°$ (c 1.02, 1N-HCl).

Example 50

Hydrolysis of Methyl L-Phenylglycinate (−)-Hemitartrate

A solution of methyl L-phenylglycinate (−)-hemitartrate mono-ethanol solvate ($[\alpha]_D + 62.4°$, 36.888 g., 0.102 mole) in 6N-hydrochloric acid (68 ml., 0.408 mole, 4 equiv.) was refluxed for 1 hour 10 minutes and then distilled for 15 minutes. Water (68 ml.) was added and the pH of the warm solution adjusted to 7.0 with ammonium hydroxide solution (0.880, 35 ml.). The mixture was cooled in ice, filtered, and the solid was washed with water (2 × 25 ml.) and ethanol (25 ml.) and dried over phosphorus pentoxide to give L-phenylglycine as white plates (13.406 g., 87%), $[\alpha]_D^{21} + 152.1°$ (c 1.007, 1N-HCl).

The product (5.968 g.) was dissolved in 2N-hydrochloric acid (130 ml.) and neutralised to pH7.0 with ammonium hydroxide solution (0.880, 26 ml.). The solid was filtered, washed, and dried as before to give L-phenylglycine (4.706 g., 79%), $[\alpha]_D^{24} + 154.7°$ (c 1.006, 1N-HCl).

The product (4.210 g.) was reprecipitated to give L-phenylglycine (3.340 g., 79%), $[\alpha]_D^{23} + 155.5°$ (c 1.005, 1N-HCl).

This product (3.002 g.) was reprecipitated to give L-phenylglycine (2.385 g., 79%, $[\alpha]_D^{22} + 152.1°$ (c 1.016, 1N-HCl), $[\alpha]_D^{23} + 153.0°$ (c 1.010, 1N-HCl).

EXAMPLE 51

Hydrolysis of Isopropyl L-Phenylglycinate (+)-Hemitartrate

A solution of isopropyl L-phenylglycinate (+)-hemitartrate hemi-ethanol solvate ($[\alpha]_D + 56.8°$, 3.540 g., 9.67 mmole) in 6N-hydrochloric acid (6.5 ml., 39.0 mmole, 4 equiv.) was refluxed for 1¼ hours. Water (6.5 ml.) was added and the pH of the warm solution adjusted to 7.0 with ammonium hydroxide solution (0.880, 2.9 ml.). The mixture was cooled in ice, filtered, and the solid was washed with water (2 × 3 ml.) and ethanol (3 ml.) and dried over phosphorus pentoxide to give L-phenylglycine as white plates (1.037 g., 71%), m.p. 235° to 238° (decomp.), $[\alpha]_D^{22} + 156.0°$ (c 1.002, 1N-HCl).

EXAMPLE 52

D-p-Hydroxyphenylglycine-Acid Hydrolysis of Ethyl D-p-Hydroxyphenylglycinate (+)-Hemitartrate A solution of ethyl D-p-hydroxyphenylglycinate (+)-hemitartrate (0.997 g., mono-methanol solvate, 2.64 mmole., $[\alpha]_D - 49.8°$) in 6N-hydrochloric acid (1.8 ml., 10.8 mmole) was refluxed for 95 minutes, then cooled and taken to pH 7.5 with ammonium hydroxide. The mixture was cooled in ice for 15 minutes, filtered, washed with water (2 × 0.5 ml.), and dried to give the D-amino acid (0.117 g., 23%), $[\alpha]_D^{21} - 154°$ (c 0.995, 1N-HCl).

The filtrate was evaporated and recrystallised from hot water to give a second crop (0.157 g., 35.5%), $[\alpha]_D^{22} - 154.3°$ (c 0.980, 1N-HCl).

EXAMPLE 53

D-m-Methoxyphenylglycine

A solution of methyl D-m-methoxyphenylglycinate (+)-hemitartrate (0.909 g., 2.45 mmole) in 6N-hydrochloric acid (1.64 ml., 9.85 mmole, 4 equiv.) was refluxed for 30 minutes. Water (2 ml.) was added and the pH of the warm solution adjusted to 7.0 with 10N-ammonium hydroxide solution. The mixture was cooled in ice, filtered, washed, and dried over phosphorus pentoxide to give the D-amino acid (0.175 g., 39.5% as needles) m.p. 185° to 189°, $[\alpha]_D^{21} - 137°$ (c 0.998, 1N-HCl). The filtrate was concentrated to give a second crop (0.200 g., 32% corr.) m.p. 178° to 181°, $[\alpha]_D^{20} - 131°$ (corrected for 0.25 mole mono-ammonium tartrate and 0.45 mole ammonium chloride), $\tau$ (F$_3$CCO$_2$H) indicated the presence of 0.25 mole mono-ammonium tartrate and 0.45 mole ammonium chloride. There was no evidence for the ester at $\tau$ 6.14 in the nmr.

EXAMPLE 54

D-p-Chlorophenylglycine

A solution of methyl D-p-chlorophenylglycinate (+)-hemitartrate (0.867 g., 2.370 mmole.) in water (20 ml.) was neutralised to pH 7.0 with 10N-ammonium hydroxide solution, and extracted into methylene chloride, which was washed, dried, and evaporated to give the D-ester as a colourless oil (0.474 g., 100%). A solution of the D-ester (0.474 g., 2.370 mmole) in 6N-hydrochloric acid (1.6 ml., 9.60 mmole, 4 equiv.) was refluxed for 75 minutes. Water (1.6 ml.) was added and the pH of the warm solution adjusted to 7.0 with 10N-ammonium hydroxide solution. The mixture was cooled in ice, filtered, washed, and dried over phosphorus pentoxide to give the D-amino acid (0.337 g., 77%), m.p. 233° to 237° (decomp.), $[\alpha]_D^{20} - 129.0°$ (c 0.993, 1N-HCl), $[M]_D^{20} - 239°$.

EXAMPLE 55

Hydrolysis of Methyl D-Phenylglycinate with 1.11 N-Sodium Hydroxide

A solution of methyl D-phenylglycinate (3.660 g., 22.2 mmole, (ca. 97% optically pure)) in 1.11 N-sodium hydroxide (40 ml., 44.4 mmole, 2.0 equiv.) was stirred for 15 minutes at 23°, (tlc showed that the hydrolysis was complete after 1 minute). The pH of the solution was adjusted to 6 with 2N-hydrochloric acid, and the solid was filtered, washed with water (2 × 7 ml.) and ethanol (7 ml.), and dried over phosphorus pentoxide to give D-phenylglycine as white plates (2.876 g., 86%), $[\alpha]_D^{24} - 156.2°$ (c 1.002, 1N-HCl), (98.5% optically pure.)

EXAMPLE 56

Hydrolysis of Ethyl D-Phenylglycinate (+)-Hemitartrate with 2.22N-Sodium Hydroxide Ethyl D-phenylglycinate (+)-hemitartrate (3.089 g., mono-ethanol solvate i.e. 8.25 mmole, $[\alpha]_D^{18} - 47.1°$, (97% optically pure)) was stirred with 2.22N-sodium hydroxide (15.0 ml., 3.33 mmole, 4.04 equiv.) for 15 minutes at 23°. An oily layer (probably free ester) was immediately formed but dissolved after 2 minutes. Tlc showed that the hydrolysis was complete after 5 minutes. The reaction was worked up in a similar manner to that described in Example 55 to give D-phenylglycine as white plates (1.061 g., 85%), $[\alpha]_D^{23} - 154.7°$ (c 1.006, 1N-HCl), (97.5% optically pure.)

EXAMPLE 57

Hydrolysis of Ethyl D-Phenylglycinate (+)-Hemitartrate with Saturated Barium Hydroxide Solution As for Example 56 but using ethyl D-phenylglycinate (+)-hemitartrate (3.072 g., mono-ethanol solvate i.e. 8.20 mmole, $[\alpha]_D^{18} - 47.1°$, (97% optically pure)) in saturated barium hydroxide solution (92 ml., ca. 0.36N, i.e. ca. 33.1 mmole, ca. 4.04 equiv.), and filtering off the barium tartrate to give D-phenylglycine as white plates (0.515 g., 41.5%), $[\alpha]_D^{23} - 156.1°$ (c 1.003, 1N-HCl), (98.5% optically pure.)

The filtrate was concentrated to give a second crop (0.788 g., 63.5%), $[\alpha]_D^{23} - 96.8°$ (c 1.017, 1N-HCl) which contained barium ions.

EXAMPLE 58

Ethyl D-p-Hydroxyphenylglycinate

The pH of a solution of ethyl D-p-hydroxyphenylglycinate (+)-hemitartrate ($[\alpha]_D - 49.6°$, 9.59 g., 25.4 mmole) in water (12 ml.) was adjusted to 7.0 at 20° with 5N-sodium hydroxide (9.7 ml., 48.5 mmole). The reaction mixture was cooled to 0°, filtered, washed (2 × 5 ml.), and dried to give the D-ester (4.60 g., 93%), as needles m.p. 127° to 130°, $[\alpha]_D^{22} - 110.4°$ (c 1.018, 1N-HCl).

The filtrate was extracted with ethyl acetate, which was dried and evaporated to give a second crop (0.105 g., 2%).

EXAMPLE 59

D-p-Hydroxyphenylglycine-Base Hydrolysis of Ethyl D-p-Hydroxyphenylglycinate (+)-Hemitartrate Ethyl D-p-hydroxphenylglycinate (+)-hemitartrate (1.352 g. mono-methanol solvate, 3.58 mmole, $[\alpha]_D - 49.6°$) was stirred with 2.22N-sodium hydroxide (6.8 ml., 15.1 mmole) at 25° for 15 minutes [all the solid (possibly the insoluble D-ester) had gone in 5 minutes]. The pH of the solution was taken from 12.5 to 5.5 with 2N-hydrochloric acid (3.5 ml.) to give a white gel which became crystalline on stirring. The solid was washed with water (2 × 0.8 ml.) and dried to give D-p-hydroxyphenylglycine (0.294 g., 49%), $[\alpha]_D^{24} - 156.8°$ (c 1.005, 1N-HCl).

The filtrate was evaporated and the solid was crystallised from boiling water to give a second crop of amino acid (0.176 g., 29%), $[\alpha]_D^{24} - 148.2°$ (c 1.026, 1N-HCl).

EXAMPLE 60

D-p-Hydroxyphenylglycine-Base Hydrolysis of Ethyl D-p-Hydroxyphenylglycinate

Ethyl D-p-hydroxyphenylglycinate (1.281 g., 6.56 mmole) was stirred at 20° with 2.22 N-sodium hydroxide (6 ml., 13.3 mmole) for 15 minutes (all the ester had dissolved within 1 minute). The pH was adjusted from 11.8 to 6.6 with 2N-hydrochloric acid (6.2 ml., 12.4 mmole) to give a gel at pH 8.5. The mixture was warmed to ca. 30° to convert the gel into dense crystals. The mixture was cooled to 0°, filtered, washed (2 × 1.0 ml.), and dried to give the D-amino acid (0.796 g., 73%), m.p. 223° to 225° (decomp.), $[\alpha]_D^{22} - 158.2°$ (c 1.015, 1N-HCl). The filtrate was evaporated and crystallised from boiling water (5.5 ml.) to give a second crop (0.164 g., 15%), $[\alpha]_D^{21} - 157.2°$ (c 1.002, 1N-HCl).

EXAMPLE 61

Ethyl L-p-Hydroxyphenylglycinate

Ethyl L-p-hydroxyphenylglycinate (−)-hemitartrate ($[\alpha]_D + 47°$, 67.11 g., ca. 0.185 mole) was suspended in water (85 ml.), most of the solid dissolving on stirring. 5N-Sodium hydroxide solution (ca. 70 ml.) was added over ca. 15 minutes to raise the pH to 7.0, precipitating the amino-ester. The mixture was stirred and cooled to 3°, filtered, washed with cold water (70 ml.), and dried at 20° in vacuo to give the L-ester (33.46 g., 93%), $[\alpha]_D + 105.5°$ (c 1.04, 1N-HCl).

EXAMPLE 62

L-p-Hydroxyphenylglycine

A mixture of ethyl L-p-hydroxyphenylglycinate (19.5 g., 0.1 mole) and 2N-sodium hydroxide solution (100 ml., 0.2 mole) was stirred at 20° for 15 minutes. Concentrated hydrochloric acid was added to adjust the pH to 8.5, the mixture was warmed to 30°, and more hydrochloric acid was added to lower the pH to 6.0. The gelatinous precipitate was cooled to 0°, stirred for 2 hours, filtered, washed with cold water (2 × 5 ml), and dried at 20° in vacuo to give the L-amino acid (11.13 g., 66.5%), $[\alpha]_D + 158°$ (c 1.01, 1N-HCl).

EXAMPLE 63

Methyl L-p-Hydroxyphenylglycinate

The pH of a solution of methyl L-p-hydroxyphenylglycinate (+)-hemitartrate (4.105 g., mono-methanol solvate i.e. 11.3 mmole, $[\alpha]_D + 94.5°$) in water (17.5 ml.) was adjusted to 7.0 with 5N-sodium hydroxide solution (4.5 ml., 22.5 mmole). The mixture was cooled, filtered, washed (2 × 2.5 ml.), and dried to give the L-ester (1.814 g., 89%), m.p. 159° – 161° (decomp. to rectangular plates which melted at 168° – 173°), $[\alpha]_D^{21} + 146.0°$ (c 1.022, 1N-HCl).

EXAMPLE 64

L-p-Hydroxyphenylglycine

Methyl L-p-hydroxyphenylglycinate (1.513 g., 8.36 mmole) was stirred at 21° with 2.22N-sodium hydroxide (7.5 ml., 16.65 mmole, 1.99 equiv.) for 15 minutes (all the ester had dissolved within one minute). The pH was adjusted from 12.0 to 6.8 with 2N-hydrochloric acid (8 ml., 16 mmole) to give a gel at pH 8.7. The mixture was warmed to ca. 35° to convert the gel into dense crystals. The mixture was cooled to 0°, filtered, washed (2 × 0.9 ml.), and dried to give the L-amino acid (1.059 g., 76%), m.p. 220°–226° (decomp.), $[\alpha]_D^{21} + 157.1°$ (c 1.018, 1N-HCl.

EXAMPLE 65

Methyl D-m-Methoxyphenylglycinate

A solution of methyl D-m-methoxyphenylglycinate (+)-hemitartrate (0.315 g., 0.850 mmole) in water (7 ml.) was neutralised to pH 7.0 with ammonium hydroxide solution, and extracted into methylene chloride, which was washed, dried, and evaporated to give the D-ester as a colourless oil (0.164 g., 99%), $[\alpha]_D^{22} - 135°$ (c 1.175, MeOH), $[M]_D^{22} - 263°$.

EXAMPLE 66

Methyl D-p-Chlorophenylglycinate

A solution of methyl D-p-chlorophenylglycinate (+)-hemitartrate (0.203 g., 0.521 mmole, $[\alpha]_D - 60.8°$) in water (5 ml.) was neutralised to pH 7.0 with 10N-ammonium hydroxide solution, and extracted into methylene chloride, which was washed, dried, and evaporated to give the D-ester as a colourless oil (0.103 g., 99%), $[\alpha]_D^{22} - 129.0°$ (c 1.098, MeOH), $[M]_D^{22} - 256°$.

EXAMPLE 67

Methyl L-p-Chlorophenylglycinate

Similar to Example 66 but using a 1:1 mixture of methyl L-p-chlorophenylglycinate (+)-hemitartrate and bis-(methyl L-p-chlorophenylglycinate) tartrate (0.207 g., contains 0.669 mmole of ester), to give the L-ester as a colourless oil (0.130 g., 97%), $[\alpha]_D^{23} + 81°$ (c 4.4, MeOH).

EXAMPLE 68

D-2-Thienylglycine

Methyl D-2-thienylglycinate (+)-hemitartrate ($[\alpha]_D - 43.6°$, 0.742 g., 2.31 mmole) was stirred with 2.22N-sodium hydroxide solution (3.45 ml., 7.65 mmole, 3.32 equiv.). The hemitartrate had dissolved after 1 minute and tlc showed that hydrolysis was complete. After 15 minutes the pH was adjusted to 6.6 with 2N-hydrochloric acid. The mixture was cooled in ice, filtered, and the solid washed with water (2 × 0.4 ml.), and dried over phosphorus pentoxide giving D-2-thienylglycine (85 mg., 23.5%), m.p. 188° to 194° (decomp.), $[\alpha]_D^{20} - 69.3°$ (c 0.8085, H$_2$O).

EXAMPLE 69

L-p-Methoxyphenylglycine

A solution of ethyl L-p-methoxyphenylglycinate (+)-hemitartrate (1.105 g., 2.92 mmole) was stirred with 2.22N-sodium hydroxide (5.5 ml., 12.2 mmole, 4.2 equiv.) for 20 minutes (tlc showed the reaction was complete after 5 minutes). The pH of the solution was taken from 12.7 to 6.1 with 2N-hydrochloric acid (2.8 ml.) to give a white solid. The solid was filtered, washed, and dried to give L-p-methoxyphenylglycine (0.436 g., 82.5%), $[\alpha]_D^{24} + 90.5°$ (c 1.010, 1N-HCl). [The product was 60% optically pure].

EXAMPLE 70

L-Methionine

Methyl L-methioninate (+)-hemitartrate ($[\alpha]_D + 29.8°$, 5.914 g., 18.9 mmole) was stirred with 5N-sodium hydroxide solution [2.514 g., 62.8 mmole, 3.32 equiv. sodium hydroxide in water (12.5 ml.)]. Most of the hemitartrate dissolved immediately but after 8 minutes a solid had precipitated (disodium (+)-tartrate). After 1 hour 35 minutes the pH of the mixture was adjusted from 12.3 to 5.8 (the isoelectric point of methionine) with concentrated hydrochloric acid — solid was present all the time. The mixture was cooled in ice, filtered, and the solid washed with water (2 × 3 ml.), and dried over phosphorus pentoxide giving L-methionine (1.928 g., 68%), m.p. decomp. 210 to 215°, darkening began at 225° but the sample did not melt below 320°. An authentic sample of L-methionine decomposed at 225° to 230°, darkening and shrinking occurred at 230° but the sample did not melt below 330°, $[\alpha]_D^{22} + 21.7°$ (c 1.007, 1N-HCl) — 4 dm. tube, and $[\alpha]_D^{22} + 21.4°$ (c 1.021, 1N-HCl) — 1 dm. tube.

EXAMPLE 71

N-Benzylidene Methyl Phenylglycinate

A solution of recrystallised methyl DL-phenylglycinate (2.073 g., 12.5 mmole) and benzaldehyde (1.33 g., 12.9 mmole, 1.03 equiv.) in benzene (50 ml.) was refluxed for 2½ hours using a Dean and Stark water removal apparatus. The clear pale yellow solution was evaporated to give a yellow semi-crystalline mass (3.4 g., 100%). A sample was crystallised from ethanol to give the Schiff base as prisms m.p. 67° to 69°.

EXAMPLE 72

Resolution with Racemisatin of Methyl-p-Hydroxyphenylglycinate with (+)-Tartaric acid in Methanol/Benzene (4:1)

Methanol (50 ml.) and benzaldehyde (2.8 ml., 27.8 mmole) was stirred and (+)-tartaric acid (4.2 g., 28 mmole) and methyl-DL-p-hydroxyphenylglycinate (5.0 g., 27.6 mmole) added. The mixture was refluxed to give a clear solution. Benzene was added to the refluxing solution until a permanent cloudiness was produced (12.5 ml. required). The suspension was stirred and allowed to cool to 27° over 2½ hours. The crystalline solid was collected by filtration, washed with methanol/benzene 1/1 (2 × 5 ml.) and dried at 40° in vacuo for 1½ hours to give methyl-D-p-hydroxyphenylglycinate -(+)-hemitartrate, hemibenzene monomethanol solvate 7.60 g. (68.5% theory) $[\alpha]_D - 65.0°$ (1.1% H$_2$O).

The filtrate and washings were combined and stirred at room temperature for a further 16 hours and a second crop was obtained 1.20 g. (10.8% theory), $[\alpha]_D - 56.4°$ (1% H$_2$O).

We claim:

1. A process for the production of an ester of one enantiomer of an α-amino acid in the form of a salt with an optically active acid, which comprises reacting an ester of the opposite enantiomer of said α-amino acid, which may be in admixture with an ester of the desired enantiomer, with said optically active acid and an aldehyde or ketone, whereby an ester of the desired enantiomer separates out in the form of the said salt.

2. A process as claimed in claim 1 wherein the said ester of one enantiomer of an α-amino acid is represented by the formula:

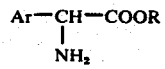
        IV wherein R represents an unsubstituted or substituted alkyl group with 1 – 6 carbon atoms, an unsubstituted or substituted cycloalkyl group with 5 or 6 carbon atoms, an aralkyl group, or an aryl group; and Ar represents an aryl group.

3. A process as claimed in claim 2 wherein a compound of formula IV is used in which Ar represents a m-hydroxyphenyl, m- methoxyphenyl, p-chlorophenyl or a m- or p-tolyl group.

4. A process as claimed in claim 2 wherein the aldehyde or ketone is represented by the formula:

$$R^2-CO-R^3 \qquad \text{III}$$

wherein $R^2$ and $R^3$, which may be the same or different, each represents a hydrogen atom or an optically substituted aliphatic, araliphatic, aromatic or heterocyclic group; or $R^2$ and $R^3$ together with the carbonyl group to which they are bonded represent a cycloalkanone.

5. A process as claimed in claim 4 in which the compound of formula III used is acetaldehyde, benzaldehyde, anisaldehyde, p-nitrobenzaldehyde, acetophenone, methyl ethyl ketone, methyl isobutyl ketone or acetone.

6. A process as claimed in claim 5 wherein the said optically active acid is (+)-tartaric acid.

7. A process as claimed in claim 6 in which the compound of formula IV used is methyl DL-phenylglycinate.

8. A process as claimed in claim 7 in which the DL-ester is reacted in the presence of (+)-tartaric acid with benzaldehyde or acetone in ethanol as solvent whereby methyl D-phenylglycinate is obtained as the (+)-hemitartaric salt.

9. A process as claimed in claim 6 in which the compound of formula IV is ethyl DL-phenylglycinate.

10. A process as claimed in claim 9 in which the DL-ester is reacted in the presence of (+)-tartaric acid with benzaldehyde or acetone in ethanol or methanol as solvent whereby ethyl D-phenylglycinate is obtained as the (+)-hemitartrate salt.

11. A process as claimed in claim 6 in which the compound of formula IV used is methyl DL-p-hydroxyphenylglycinate.

12. A process as claimed in claim 11 in which the DL-ester is reacted in the presence of (+)-tartaric acid with benzaldehyde in acetonitrile or in methanol/benzene as solvent whereby methyl D-p-hydroxyphenylglycinate is obtained as the (+)-hemitartrate salt.

13. A process as claimed in claim 6 in which the compound of formula IV used is ethyl DL-p-hydroxyphenylglycinate.

14. A process as claimed in claim 13 in which the DL-ester is reacted in the presence of (+)-tartaric acid with benzaldehyde in methanol/methylene chloride as solvent or with acetone in methanol as solvent whereby ethyl D-p-hydroxyphenylglycinate is obtained as the (+)-hemitartrate salt.

15. A process as claimed in claim 2 wherein the ester of the enantiomer of the α-amino acid, which may be in the form of a salt with the optically active acid, thus obtained is hydrolysed in an aqueous solution of a strong acid, optionally after preliminary conversion of said salt to the free base, whereby the desired enantiomer of the α-amino acid is obtained in the form of a salt thereof.

16. A process as claimed in claim 2 wherein the ester of the enantiomer of the α-amino acid, which may be in the form of a salt with the optically active acid, thus obtained is hydrolysed in an aqueous solution of a strong base, optionally after conversion of the said salt to the free base, whereby the desired enantiomer of the α-amino acid or a salt thereof is obtained.

17. A process as claimed in claim 1 wherein the said ester of one enantiomer of an α-amino acid is represented by the formula:

$$R^1-\underset{NH_2}{\underset{|}{CH}}-COOR \qquad \text{II}$$

wherein $R^1$ is optionally substituted alkyl, aralkyl, or cycloalkyl group and R represents an unsubstituted or substituted alkyl group with 1–6 carbon atoms, an unsubstituted or substituted cycloalkyl group with 5 or 6 carbon atoms, an aralkyl group or an aryl group.

18. A process as claimed in claim 1 wherein the said ester is an ester of a naturally occurring α-amino acid.

* * * * *